United States Patent [19]

Felder et al.

[11] Patent Number: 5,023,379
[45] Date of Patent: Jun. 11, 1991

[54] PROCESS FOR THE PREPARATION OF HYDROXYAMINES

[75] Inventors: Ernst Felder, Riva San Vitale, Switzerland; Michael Römer, Rodgau, Fed. Rep. of Germany; Hans Bardonner, Bad König, Fed. Rep. of Germany; Hartmut Härtner, Mühltal, Fed. Rep. of Germany; Wolfgang Fruhstorfer, Mühltal-Traisa, Fed. Rep. of Germany

[73] Assignee: Merck Patent Gesellschaft mit beschraenkter Haftung, Darmstadt, Fed. Rep. of Germany

[21] Appl. No.: 492,018

[22] Filed: Mar. 12, 1990

Related U.S. Application Data

[63] Continuation of Ser. No. 30,775, Mar. 25, 1987, abandoned.

[30] Foreign Application Priority Data

Mar. 25, 1986 [DE] Fed. Rep. of Germany ....... 3609978

[51] Int. Cl.$^5$ .................. C07C 209/26; C07C 213/00

[52] U.S. Cl. ................... 564/472; 564/473; 564/480; 564/489

[58] Field of Search ................ 564/472, 473, 480, 489

[56] References Cited

U.S. PATENT DOCUMENTS 3,448,153 6/1969 Cavitt et al. ..................... 564/472
4,041,080 8/1977 Goethel et al. .................. 564/473

Primary Examiner—Richard L. Raymond
Attorney, Agent, or Firm—Millen, White & Zelano

[57] ABSTRACT

A process for the production of hydroxyamines of the formula I $$R^1-CH(OH)-CH(NHR^3)-R^2 \qquad (I)$$

wherein
$R^1$ and $R^2$ independently of one another are H or $CH_2OH$ and
$R^3$ is H, $C_1-C_4$-alkyl or $C_1-C_4$-hydroxyalkyl comprising reacting an oxo compound with an amine and reducing the resultant ketimine with a reducing agent.

24 Claims, No Drawings

PROCESS FOR THE PREPARATION OF HYDROXYAMINES

This is a continuation of application Ser. No. 07/030,775 filed Mar. 25, 1987, now abandoned.

BACKGROUND OF THE INVENTION

This invention relates to processes for the preparation of hydroxyamines of the formula I $$R^1-CH(OH)-CH(NHR^3)-R^2 \qquad (I)$$

wherein
$R^1$ and $R^2$ independently of one another are H or $CH_2OH$ and
$R^3$ is H, $C_1$-$C_4$-alkyl or $C_1$-$C_4$-hydroxyalkyl.

Hydroxyamines of the formula I constitute valuable intermediates for the preparation of active compounds for medicaments. Thus, for example, 2-amino-1,3-propanediol (serinol) is used for the preparation of the X-ray contrast medium Iopamidol [N,N'-bis-[2-hydroxy-1-(hydroxymethyl)-ethyl]-2,4,6-triiodio-5-lactamidoisophthalamide].

A large number of processes are known for the preparation of hydroxyamines of the formula I. Thus, these compounds can be prepared by reducing corresponding nitro or oximino derivatives of amino acids or esters thereof or of oximinodicarboxylic acid esters. The reaction of formaldehyde with suitable monohydroxyamines in the presence of certain microorganisms, or the sulfation of glycerol, followed by ammonolysis, are also known. EP 0,025,083 discloses, in addition to hydrogenation processes, a method of preparation starting from epichlorohydrin, which is carcinogenic.

The processes of synthesis described have, however, a number of disadvantages. Either the yields are unsatisfactory, or the starting materials are expensive or only accessible by a complicated route, or have a very adverse effect on health, or by-products are produced for example salts which can be removed with difficulty or only with considerable effort.

A process for the preparation of 2-amino-1,3-propanediol by hydrogenating dihydroxyacetone in the presence of ammonia and a reducing agent is disclosed in German Patent 2,829,916. However, this process gives acceptable yields of about 60% of theory only on a small scale, in laboratory tests. With larger reaction batches, suitable for industrial production, the achievable yield and quality of the product fall off greatly because of appreciable formation of by-products. In addition, the catalyst employed can in most cases not be reused further owing to its activity being reduced by the by-products formed.

SUMMARY OF THE INVENTION

An object of this invention is to provide a process for the preparation of hydroxyamines of formula I which does not possess the disadvantages of the known processes, or has them only to a small extent.

Upon further study of the specification and appended claims, further objects and advantages of this invention will become apparent to those skilled in the art.

These objects have been achieved by a process wherein hydroxyamines of the formula I are advantageously obtained by reacting an oxo compound with an amine to give a ketimine and subsequently treating the latter with a reducing agent. The yields in this process are excellent, and work-up is carried out very simply, since only very small amounts of by-products are formed or none at all.

The invention involves a process for the preparation of hydroxyamines of the formula I, comprising reacting an oxo compound of the formula II $$R^1-CH(OH)-CO-R^2 \qquad (II)$$

wherein $R^1$ and $R^2$ have the meaning indicated for formula I,
with an amine $R^3-NH_2$,
wherein $R^3$ has the meaning indicated for formula I, to give a ketimine of the formula III $$R^1-CH(OH)-C(=NR^3)-R^2 \qquad (III)$$

wherein $R^1$, $R^2$ and $R^3$ have the meanings indicated for formula I.

This ketimine is then treated with a reducing agent.

Surprisingly, the two-step process procedure according to the invention, with its longer reaction times in comparison with the single-stage process of German Patent 2,829,916, exhibits virtually no formation of by-products and hence considerably better yields and higher purity values of the hydroxyamines of the formula I.

The first step, the reaction of an oxo compound with an amine, is carried out at a temperature of about $-80°$ to $+30°$ C., preferably about $-15°$ to $+15°$ C. and under pressures of about 1-200 bar, preferably 1-100 bar. During the first reaction step, the amine compound is normally in excess and is present in an amount of 100-600, preferably 200-400 mole %, based on the moles of the oxo compound. The product obtained by this first step can be treated in situ within the reaction mixture with a reducing agent without isolation.

It is preferable to carry out the reactions under pressures of about 1-300 bar, preferably about 50-150 bar, and at temperatures of about 0°-200° C., preferably about 40°-90° C.

The amines of the formula $R^3$-$NH_2$ can be employed in the reaction, preferably in excess, in liquid or gaseous form or dissolved in an inert solvent. Preferred solvents are alcohols, such as methanol, ethanol or isopropanol; further examples of suitable solvents are water, ethers, such as tetrahydrofuran or dioxane, or mixtures of these solvents.

The reducing agent used is preferably hydrogen in the presence of a metal catalyst. Preferred metals are nickel and also cobalt and noble metals, such as platinum, rhodium, palladium or ruthenium. Nickel and cobalt catalysts are preferably employed in the form of Raney metals, while the noble metal catalysts are preferably employed in the form of support catalysts (for example, platinum, rhodium or palladium on charcoal, calcium carbonate, aluminum oxide or strontium carbonate), in the form of oxides (for example, platinum, or palladium oxide) or in a finely divided form (for example, platinum black). The amount of catalyst to be used is about 1 to 100 percent by weight, relative to the starting material of the formula II.

Other reducing agents such as metal hydrides, e.g., lithium aluminum hydride, sodium borohydride can be used too.

The addition of ammonium salts, for example, ammonium chloride or acetate, can be advantageous; it is preferable to use about 0.1 to 1.5 mol of ammonium salt, relative to 1 mol of starting material of the formula II (i.e., about 10-150 mol %).

Work-up in the process according to the invention is very simple: the catalyst is filtered off, the filtrate is evaporated, and the resulting base of formula I is purified by distillation or by conversion into one of its salt and then the crystallization of the salt. The catalyst which has been filtered off can be used again without loss of activity.

The invention thus makes available a very advantageous process for preparing, in a simple manner and in high yields, hydroxyamines of the formula I, in particular for preparing 2-amino-1,3-propanediol, from carbonyl compounds of the formula II and amines of the formula $R^3$-$NH_2$.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLE 1

103.6 kg of dihydroxyacetone and 230 l of methanol are placed in a 1200 l apparatus and are cooled to +10° C. 55 kg of liquid ammonia are introduced at an internal temperature not higher than 20° C., in the course of which the dihydroxyacetone dissolves. Stirring is continued for 1 hour at room temperature. 100 kg of moist Raney nickel catalyst is then added to the reaction mixture, and the apparatus is pressurized with a hydrogen atmosphere at 100 bar. The hydrogenation is complete after stirring for 40 minutes at 70° C. The mixture is cooled and the catalyst is removed by filtration. The filtrate is evaporated to dryness under reduced pressure; the residue is 105 kg of crude serinol (purity according to gas chromatography: 99%; 99% of theory).

The product is purified by conversion into the oxalate with oxalic acid dihydrate; yield 136.5 kg (87.2% of theory); m.p.: 193-195°.

EXAMPLE 2

The reaction is carried out analogously to Example 1, but using as starting material a corresponding equivalent of erythrulose. This gives a mixture of 2-deoxy-2-aminothreitol and 2-deoxy-2-aminoerythritol in a total yield of 89.4% of theory.

EXAMPLE 3

The corresponding ketimine is obtained analogously to Example 1 from glyceraldehyde and ammonia in water. After 10% by weight, relative to the amount of glyceraldehyde, of a 10% palladium/active charcoal catalyst has been added, hydrogenation is carried out at 50° and a hydrogen pressure of 65 bar. The mixture is filtered and evaporated and the residue is distilled, giving 1-amino-2,3-propanediol in a yield of 94.5% of theory.

EXAMPLE 4

A mixture of 170 kg of dihydroxyacetone, 138 kg of ethanolamine and 1400 l of methanol is stirred at room temperature for two hours. 150 kg of Raney nickel are then added to the reaction mixture, and hydrogenation is carried out for 2 hours under a hydrogen pressure of 100 bar and at 40° until the absorption of hydrogen ceases. The catalyst is filtered off, the filtrate is evaporated under reduced pressure and the residue is subjected to distillation. 2-[(2-hydroxethyl)-amino]-1,3-propanediol passes over at 152°-157°/0.001 mm (224 kg; 88% of theory).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a hydroxyamine of formula I $$R^1\text{---}CH(OH)\text{---}CH(NHR^3)\text{---}R^2 \quad (I)$$

wherein
$R^1$ and $R^2$ are each $CH_2OH$ and one of $R^1$ and $R^2$ can also be H, and
$R^3$ is H, $C_1$-$C_4$-alkyl or $C_1$-$C_4$-hydroxyalkyl, comprising reacting an oxo compound of formula II $$R^1\text{---}CH(OH)\text{---}CO\text{---}R^2 \quad (II)$$

with an amine of the formula $R^3$-$NH_2$ to obtain an intermediate and then reducing said intermediate with a reducing agent.

2. A process according to claim 1, wherein said hydroxyamine is 2-amino-1,3-propanediol.

3. A process according to claim 2, wherein said oxo compound is 1,3-dihydroxyacetone and said amine is ammonia.

4. A process according to claim 1, wherein said reducing agent is hydrogen in the presence of a metal catalyst.

5. A process according to claim 4, wherein said metal is nickel, cobalt or a noble metal.

6. A process according to claim 4, wherein said metal catalyst is a nickel or cobalt Raney catalyst.

7. A process according to claim 4, wherein said metal catalyst is a noble metal on a support.

8. A process according to claim 4, wherein said metal catalyst is a noble metal selected from platinum, rhodium, or palladium on a support selected from charcoal, calcium carbonate, aluminum oxide or strontium carbonate.

9. A process according to claim 4, wherein said metal catalyst is a noble metal oxide.

10. A process according to claim 4, wherein said metal catalyst is employed in an amount of about 1-100% by weight of the amount of oxo compound used.

11. A process according to claim 1, wherein reduction of said intermediate is performed at a pressure of about 1-300 bar.

12. A process according to claim 1, wherein reduction of said intermediate is performed at a pressure of about 50-150 bar.

13. A process according to claim 1, wherein reduction of said intermediate is performed at a temperature of about 0°-200° C.

14. A process according to claim 1, wherein reduction of said intermediate is performed at a temperature of about 40°-90° C.

15. A process according to claim 1, wherein said oxo compound is reacted with said amine in the presence of an ammonium salt.

16. A process according to claim 1, wherein said amine is dissolved in an inert solvent.

17. A process for the preparation of a hydroxamine of formula I $$R^1-CH(OH)-CH(NHR^3)-R^2 \quad (I)$$

wherein
R$^1$ and R$^2$ are each CH$_2$OH and one of R$^1$ and R$^2$ can also be H, and
R$^3$ is H, C$_1$-C$_4$-alkyl or C$_1$-C$_4$-hydroxalkyl, comprising reducing the product of the reaction of an oxo compound of formula II $$R^1\text{-CH(OH)-CO-}R^2 \quad (II)$$

with an amine of the formula R$^3$-NH$_2$.

18. A process according to claim 1, wherein the reaction of said oxo compound with said amine is carried out at a temperature of about −80° to +30° C. and under a pressure of about 1-200 bar.

19. A process according to claim 1, wherein, during the reaction of said oxo compound with said amine, said amine is present in an amount of 200-400 mole % based on the amount of moles of said oxo compound.

20. A process according to claim 1, wherein the intermediate obtained from the reaction of said oxo compound with said amine is treated with said reducing agent in situ within the reaction mixture without isolation.

21. A process for the preparation of a hydroxamine of formula I $$R^1-CH(OH)-CH(NHR^3)-R^2 \quad (I)$$

wherein
R$^1$ and R$^2$ are each CH$_2$OH and one of R$^1$ and R$^2$ can also be H, and
R$^3$ is H, C$_1$-C$_4$-alkyl or C$_1$-C$_4$-hydroxalkyl, consisting essentially of the steps of (1) reacting an oxo compound of formula II $$R^1-CH(OH)-CO-R^2 \quad (II)$$

with an amine of the formula R$^3$-NH$_2$ to obtain an intermediate and (2) reducing said intermediate with a reducing agent.

22. A process for the preparation of a hydroxamine of formula I $$R^1-CH(OH)-CH(NHR^3)-R^2 \quad (I)$$

wherein
R$^1$ and R$^2$ are each CH$_2$OH and one of R$^1$ and R$^2$ can also be H, and
R$^3$ is H, C$_1$-C$_4$-alkyl or C$_1$-C$_4$-hydroxalkyl, consisting of the steps of (1) reacting an oxo compound of formula II $$R^1-CH(OH)-CO-R^2 \quad (II)$$

with an amine of the formula R$^3$-NH$_2$ to obtain an intermediate and (2) reducing said intermediate with a reducing agent.

23. A process according to claim 21, wherein the intermediate obtained from the reaction of said oxo compound with said amine is treated with said reducing agent in situ within the reaction mixture without isolation.

24. A process according to claim 22, wherein the intermediate obtained from the reaction of said oxo compound with said amine is treated with said reducing agent in situ within the reaction mixture without isolation.

* * * * *